US008827982B2

(12) United States Patent
Goode et al.

(10) Patent No.: US 8,827,982 B2
(45) Date of Patent: Sep. 9, 2014

(54) PRE-FORMED DELIVERY CATHETERS (75) Inventors: Johnson E. Goode, Austin, TX (US);
Melissa Gene Tanner Christie,
Andover, MN (US); Stanten C. Spear,
Arden Hills, MN (US); **Rick D.
McVenes**, Isanti, MN (US)

(73) Assignee: Medtronic, Inc., Minneapolis, MN (US)

( * ) Notice: Subject to any disclaimer, the term of this patent is extended or adjusted under 35 U.S.C. 154(b) by 1664 days.

(21) Appl. No.: 11/680,194

(22) Filed: Feb. 28, 2007

(65) Prior Publication Data
US 2008/0208166 A1   Aug. 28, 2008

(51) Int. Cl.
*A61M 25/00* (2006.01)
*A61M 25/06* (2006.01)

(52) U.S. Cl.
CPC ....... *A61M 25/0662* (2013.01); *A61M 25/0041* (2013.01); *A61M 25/0053* (2013.01)
USPC .......................... 604/530; 604/523

(58) Field of Classification Search
CPC ............ A61M 25/00; A61M 25/0021; A61M 25/0041; A61M 25/0102; A61M 25/0152; A61M 25/0662
USPC ................................. 604/523–532
See application file for complete search history.

(56) References Cited

U.S. PATENT DOCUMENTS

| 4,991,578 | A | 2/1991 | Cohen |
| 5,879,296 | A | 3/1999 | Ockuly et al. |
| 6,066,126 | A | 5/2000 | Li et al. |
| 6,231,518 | B1 | 5/2001 | Grabek et al. |
| 6,245,054 | B1 | 6/2001 | Fuimaono et al. |
| 6,277,107 | B1 | 8/2001 | Lurie et al. |
| 7,065,394 | B2 | 6/2006 | Hobot et al. |
| 2004/0102830 | A1* | 5/2004 | Williams ............... 607/125 |
| 2005/0182465 | A1 | 8/2005 | Ness |

OTHER PUBLICATIONS

Williams, Terrell, "Delivery Catheter", U.S. Appl. No. 11/273,978, filed Nov. 15, 2005.
Smits, Karel, "Medical Electrode Delivery Tool", U.S. Appl. No. 11/321,390, filed Dec. 29, 2005.
Website: PeriVacTM Pericardiocentesis Kits, Boston Scientific—Electrophysiology, http://www.bostonscientific.com/sl/medical-divices-procedures/03591-pervac-pericardioe . . . , pulled from website on Feb. 7, 2007.

* cited by examiner

*Primary Examiner* — Nathan R Price (57) ABSTRACT

A delivery catheter includes a pre-formed and resilient heart-wrapping segment. The segment may have a relaxed span that allows the segment to wrap around a left side of a heart from an anterior epicardial surface to a posterior epicardial surface, when the catheter is advanced along the epicardial surface, having been inserted from a sub-xiphoid access site.

25 Claims, 9 Drawing Sheets

PRE-FORMED DELIVERY CATHETERS

TECHNICAL FIELD

The present invention pertains to catheters and more particularly to delivery catheters having lumens for delivering medical devices therethrough.

BACKGROUND

Delivery catheters are often used to position medical devices, for example, one or more medical electrodes, at implant sites within a body of a patient, via minimally invasive techniques. These catheters are constructed having a lumen, which provides a pathway to the implant site, through which an implanting physician may pass the medical device without encountering anatomical obstructions. Some delivery catheters include mechanisms, such as pull-wire actuation, which allow the implanting physician to actively change a curvature of the catheter in order to direct a distal tip of the catheter to a target implant site; while other delivery catheters have pre-formed curvatures tailored to position a distal tip thereof at a particular anatomical site from a particular percutaneous access site, thus eliminating the need to actively control the curvature during the implant procedure.

In certain instances, a patient suffering from bradycardia, tachyarrhythmia and/or heart failure will benefit from electrical stimulation pacing and/or defibrillation electrodes implanted on an epicardial surface of the patient's heart. Minimally invasive methods for accessing the epicardial surface have been developed; these methods may be used by way of a mini-thoracotomy, or in conjunction with a trocar, a cannula or a needle that has been passed, via a percutaneous incision, through an interstitial space between the patient's ribs, or via a percutaneous puncture, or stick at a sub-xiphoid location.

U.S. Pat. No. 4,991,578 describes a method for gaining access to an epicardial surface of a heart, wherein a percutaneous needle is inserted at a sub-xiphoid location until the tip of the needle pierces through a pericardial sac surrounding the heart; a guide wire is then inserted, through a lumen of the needle, into the pericardial space over the epicardium, and the needle is removed. An introducer sheath or a delivery catheter may be inserted over the guide wire into the pericardial space to provide access to the epicardial surface of the heart.

Once access to the epicardial surface is established, for example, by means of tools provided in a pericardiocentesis kit, the implanting physician may insert a medical device, for example, a medical electrical lead, into the pericardial space. The physician will almost always need to direct the medical device within the pericardial space to a specific epicardial site where stable and effective medical therapy, according to the patient's needs, can be delivered from the device. Thus there is a need for delivery catheters formed to facilitate the delivery of medical devices to specific epicardial implant sites.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

DETAILED DESCRIPTION

The following detailed description is exemplary in nature and is not intended to limit the scope, applicability, or configuration of the invention in any way. Rather, the following description provides practical illustrations for implementing exemplary embodiments of the present invention. Examples of constructions, materials, dimensions, and manufacturing processes are provided for selected elements, and all other elements employ that which is known to those of skill in the field of the invention. Those skilled in the art will recognize that many of the examples provided have suitable alternatives that can be utilized.

Figure 1A:
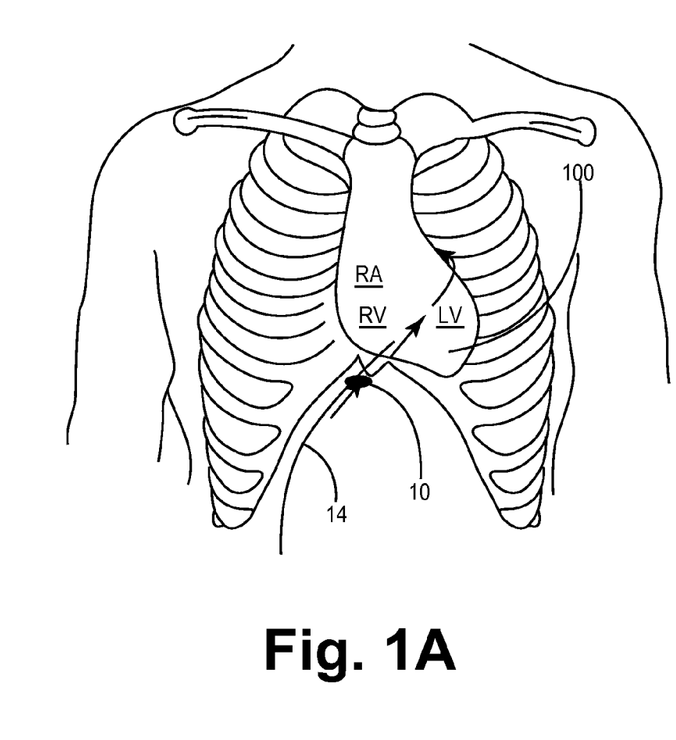
FIG. 1A is a schematic anterior view of a heart within a chest, wherein a pathway over an epicardial surface, from a sub-xiphoid access site, is depicted.
Figure 1B:
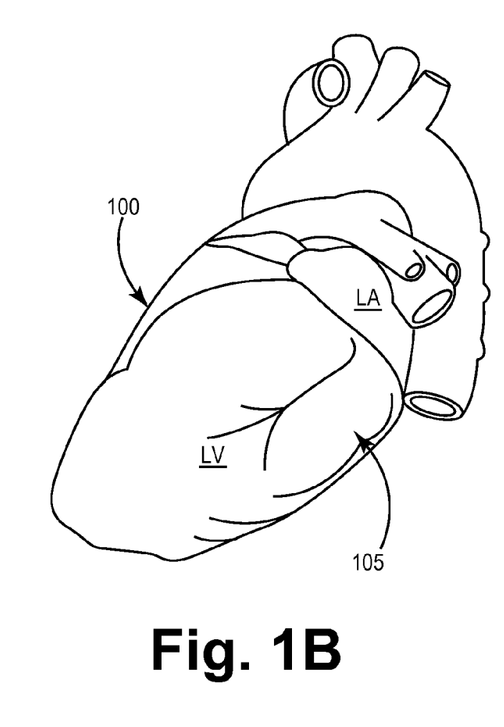
FIG. 1B is a left lateral view of the heart.

FIG. 1A is a schematic anterior view of a heart 100 within a chest of a patient. FIG. 1A illustrates a percutaneous sub-xiphoid access site 10, which provides access to an epicardial surface of heart 100, and which may have been formed, as described above, via a percutaneous needle stick. Passage for an introducer sheath or a delivery catheter, through site 10, to an epicardial surface of heart 100 may be provided by a guide wire 14, having been passed through a lumen of the needle. FIG. 1A further illustrates indicators of locations of some chambers of the heart 100, a right atrium RA, a right ventricle RV, and a left ventricle LV, for reference, along with a general pathway, per the arrows, into access site 10, for example, via guide wire 14, and along the anterior epicardial surface and around a left lateral side of the heart to a target site. According to embodiments of the present invention, a delivery catheter, having a pre-formed curvature and a longitudinally extending lumen, provides for passage of a medical device, for example, a medical electrical lead, to the target site, which is located along a posterior lateral aspect of heart 100, for example, in a zone indicated by reference number 105 in FIG. 1B, which is a left lateral view of heart 100. Zone 105, which is in proximity to a base of the LV, has been demonstrated to include effective left ventricular pacing sites. The delivery catheter may be advanced to zone 105, for example, generally according to the pathway shown in FIG. 1A, preferably, within the pericardial space, beneath the pericardial sac, or over the pericardial sac, where access to within the pericardial space may be provided, for example, via puncturing with a tool delivered through the catheter.

Figure 2:
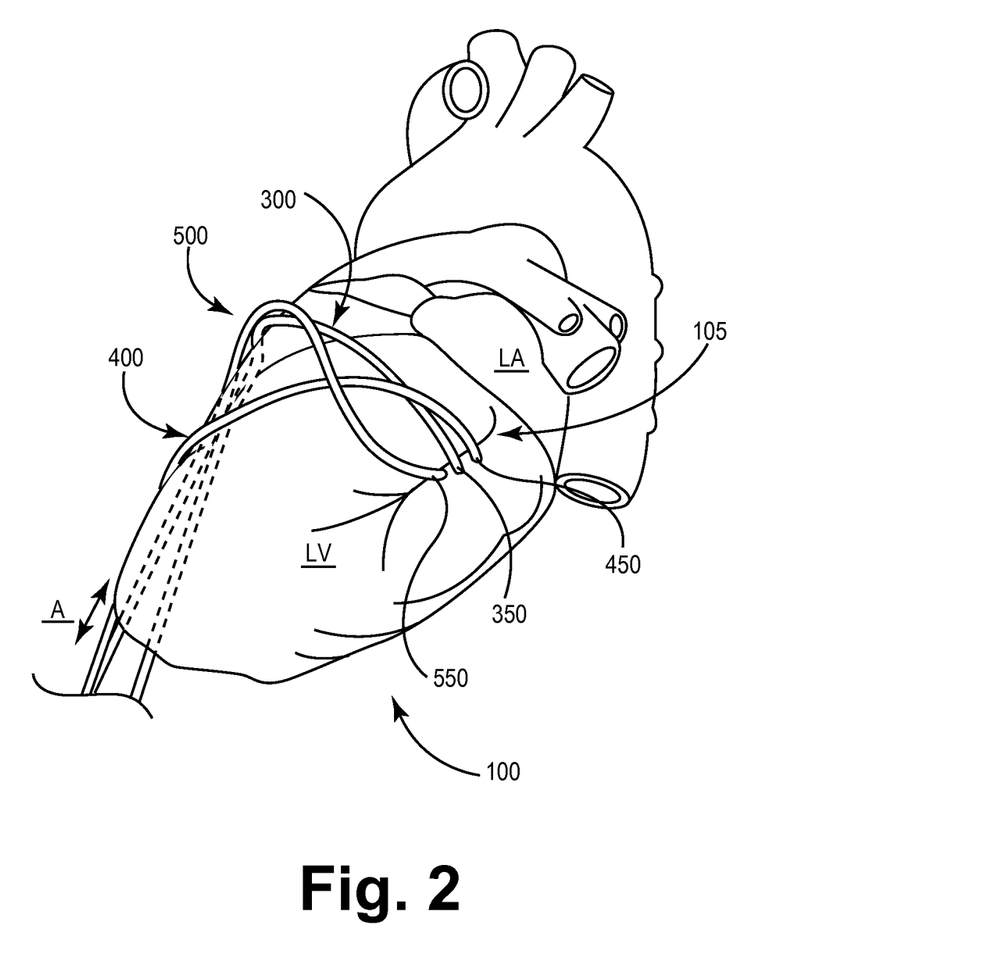
FIG. 2 is a schematic left lateral view of some delivery catheters wrapped about the heart, according to some alternate embodiments of the present invention.

FIG. 2 is a schematic left lateral view of delivery catheters 300, 400 and 500 hugging, or wrapped about heart 100, according to some alternate embodiments of the present invention. FIG. 2 illustrates distal portions of all catheters 300, 400, 500 in order to compare various alternative approaches to zone 105 facilitated by each of catheters 300, 400, 500, having been inserted at access site 10 (FIG. 1A); each distal portion of catheters 300, 400, and 500 is shown terminated by a distal tip 350, 450, and 550, respectively, which is disposed at a target site in zone 105. (It should be noted that all of catheters 300, 400, 500 are included in FIG. 2 in order to illustrate various embodiments of the present invention side-by-side, and it is not preferred that more than one catheter at a time be inserted to carry out methods of the present invention.) Each distal portion of catheters 300, 400 and 500 includes a curvature, which is pre-formed, according to manufacturing methods known to those skilled in the art, and which facilitates the wrapping about heart 100 and the positioning of tips 350, 450, 550; each catheter 300, 400, 500 will be described in greater detail below.

Figure 1C:
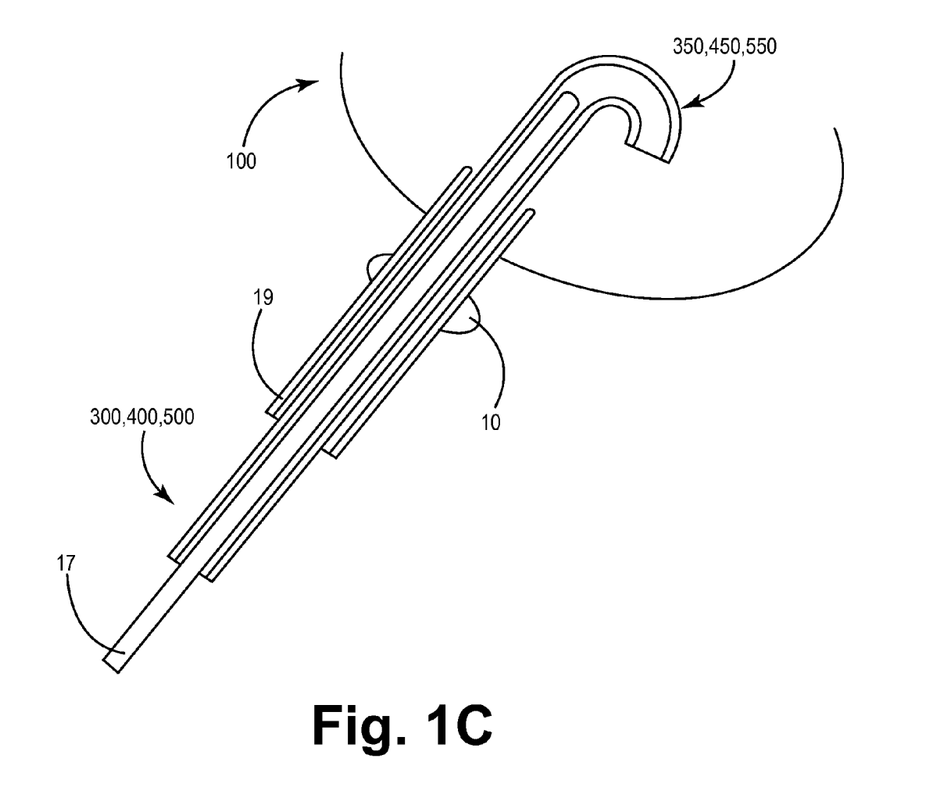
FIG. 1C is a detailed section view of the access site of FIG. 1A, wherein a delivery catheter is shown inserted, according to some embodiments of the present invention.

When a catheter of the present invention, for example, any of catheters 300, 400, 500, is initially inserted from access site 10, for example as is illustrated in FIG. 1C, an elongate and relatively rigid element 17 may be disposed within a lumen of the catheter in order to straighten the pre-formed curvature thereof. FIG. 1C illustrates any one of catheters 300, 400, 500 having element 17 inserted therein to straighten the pre-formed curvature thereof; FIG. 1C further illustrates any one of catheter distal tips 350, 450, 550, which extends distally from the straightened pre-formed curvature, having a relatively tight bend formed therein that will be described in greater detail below. According to some methods of the present invention, wherein straightening element 17 is employed, an operator, or implanting physician, may pull element 17 back, proximally, or advance the catheter distally beyond the element, once the catheter has been advanced into the pericardial space, in order to release the pre-formed curvature of the catheter while advancing the catheter along the anterior portion of the epicardial surface and around the left lateral side; the re-formed or released pre-formed curvature causes the catheter to wrap about the heart in a fashion similar to that illustrated for catheters 300, 400, 500 in FIG. 2. Straightening element 17 may include a longitudinally extending lumen so that element 17 may be passed over guide wire 14 (FIG. 1A), previously inserted at site 10, or the catheter and straightening element 17, inserted therein, may be passed through an introducer sheath 19, which has been inserted over guide wire 14. Although not necessary, such an introducer sheath may have a lumen sized to accommodate guide wire 14 and any of catheters 300, 400, 500; some embodiments of introducer sheaths may have a dual lumen construction, one lumen accommodating the guide wire and another, the catheter. According to alternate methods, introducer sheath 19 serves to straighten the pre-formed curvature of the catheter, for example, one of catheters 300, 400, 500, for initial insertion into the pericardial space; the catheter is allowed to re-assume its pre-formed shape as the catheter is advanced toward the left lateral side of the heart, beyond a distal end of introducer sheath 19, which may be disposed anywhere within the pericardial space.

With reference to FIG. 2, it may be appreciated that, once catheters 300, 400, 500 are wrapped about the heart, so that distal tips 350, 450, 550 are positioned toward the posterior side of heart 100, catheters 300, 400, 500 may be pushed and/or pulled, per arrow A, and/or twisted, or "torqued", in order to adjust a position of tips 350, 450, 550 in zone 105. Those skilled in the art will further appreciate that sidewalls of catheters 300, 400, 500 are constructed, according to methods known to those skilled in the art, for transmission of push and torsional forces applied to proximal ends thereof, which are disposed outside the chest of the patient. According to preferred methods, wherein catheters are advanced from access site 10, within the pericardial space, it will be further appreciated that the pericardial sac overlying the epicardial surface of heart 100 provides a kind of holding force over catheters 300, 400, 500, which that may further facilitate the placement of catheter distal tips 350, 450, 550.

According to preferred embodiments of the present invention, tips 350, 450, 550, which extend distally from the pre-formed curvatures of catheters 300, 400, 500, are pre-formed in a relatively tight bend, for example, having a radius less than approximately 2 cm (0.78"), preferably approximately 1.75 cm (0.69"), such that the outer surface of the bend is a leading edge, when the pre-formed curvatures of catheters 300, 400, 500 are straightened, for example, as described above and illustrated in FIG. 1C, for initial advancement over the epicardial surface. The relatively tight bend can facilitate smooth forward passage of the catheter by preventing tips 350, 450, 550 from being directed outward, toward the pericardial sac surrounding the epicardial surface, and/or from being directed inward toward the epicardial surface, as catheters 300, 400, 500 are advanced over the epicardial surface. According to those methods, described above, which employ straightening element 17, straightening element 17 may be advanced within the lumen of the catheter only to a point proximal the relatively tight bend, which is pre-formed in the distal tip of the preferred embodiment, so that the tight bend is not straightened by element 17, for example, as is illustrated in FIG. 1C. However, it should be noted that straightening element 17 may be positioned in any location along a length of the catheter to achieve a desired stiffness and/or a desired straightening of the catheter for initial insertion.

Sidewalls of catheters 300, 400, 500 may be formed from any suitable biocompatible flexible and resilient material known to those skilled in the art, an example of which is Pebax® reinforced with a stainless steel metal braid. Although the scope of the present invention is not limited by a particular outer diameter of catheter sidewalls, a suitable range of outer diameters may extend from approximately 5F (0.065") to approximately 12F (0.156"). Catheter tips 350, 450, 550 may be an integral extension of the corresponding catheter sidewall or formed from another material coupled to the sidewall, for example, a relatively low durometer of Pebax®, silicone, or polyurethane. According to some preferred embodiments of the present invention, a stiffness of catheters 300, 400, 500 may vary along a length thereof, such that catheters 300, 400, 500 have an increased flexibility in proximity to tips 350, 450, 550; according to an exemplary embodiment of the present invention, stainless steel braid-reinforced sidewalls of catheters 300, 400, 500 are formed with up to seven Pebax® materials having durometers ranging from approximately 69D, in proximity to a proximal end of catheters 300, 400, 500, to approximately 25D at distal tips 350, 350, 550. In order to facilitate fluoroscopic navigation of catheters 300, 400, 500, catheter tips 350, 450, 550 may include a radiopaque marker, either coupled thereto, for example, a platinum band, or embedded therein, for example, a barium sulfate powder blended into a polymer forming the tips. According to some embodiments, in order to facilitate either fluoroscopic or ultrasonic navigation, catheters 300, 400, 500 include one or more radiopaque and echogenic markers formed by incorporation of tungsten carbide into at least a portion of the sidewalls thereof, for example, as is described in commonly assigned U.S. Pat. No. 7,065,394, salient portions of which are hereby incorporated by reference. Any of tips 350, 450, 550 may include at least one electrode mounted thereto and coupled to a corresponding electrical contact at a proximal end of catheters 300, 400, 500, via a conductor extending within or alongside the sidewall thereof; the at least one electrode can, by sensing and/or stimulating, facilitate selection of an appropriate site for electrical stimulation, for example, left ventricular pacing, the stimulation site at which any of tips 350, 450, 550 may disposed for delivery of a pacing lead thereto.

Figure 3A:
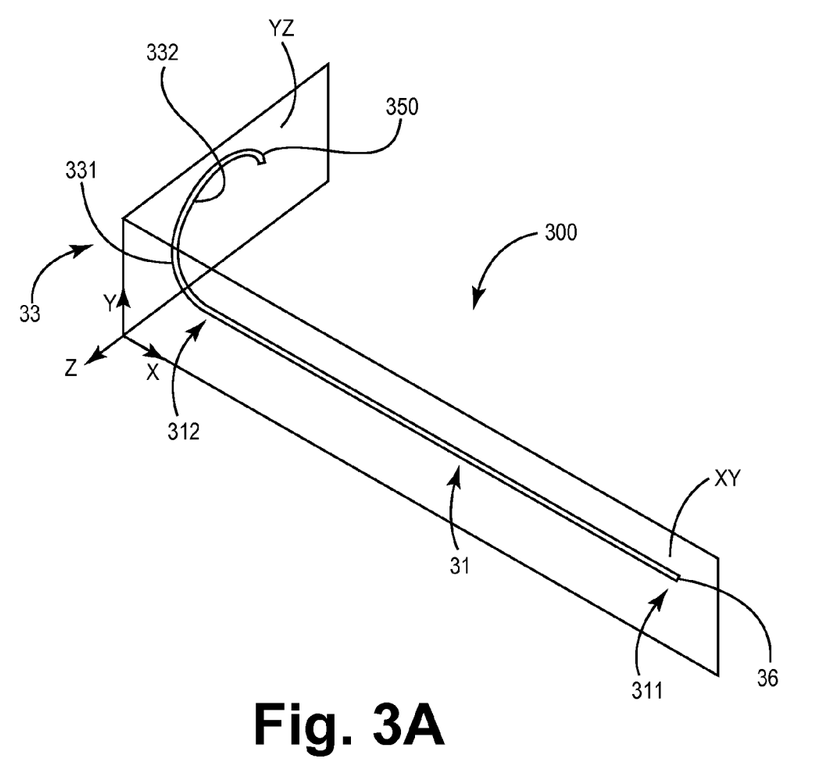
FIG. 3A is perspective view of a delivery catheter, according to some embodiments of the present invention.

FIG. 3A is perspective view of delivery catheter 300, according to some embodiments of the present invention. FIG. 3A illustrates catheter 300 including a relatively straight proximal segment 31, which extends from a proximal end 311 to a distal end 312, and a pre-formed curvature, or curved distal segment 33, which extends from distal end 312 of proximal segment 31. According to the illustrated embodiment, a lumen 36 extends from proximal end 311 through distal tip 350 in order to provide a passageway for delivery of a medical device such as a medical electrical lead. FIG. 3A further illustrates distal segment 33 including a first curve 331 extending in a first plane XY, and a second curve 332 extending in a second plane YZ, which is approximately orthogonal to first plane XY and to another plane formed by X and Z axes; distal tip 350 is shown extending distally from second curve 332, and, as was previously described for preferred embodiments, is shown formed in a relatively tight bend.

Figure 3B:
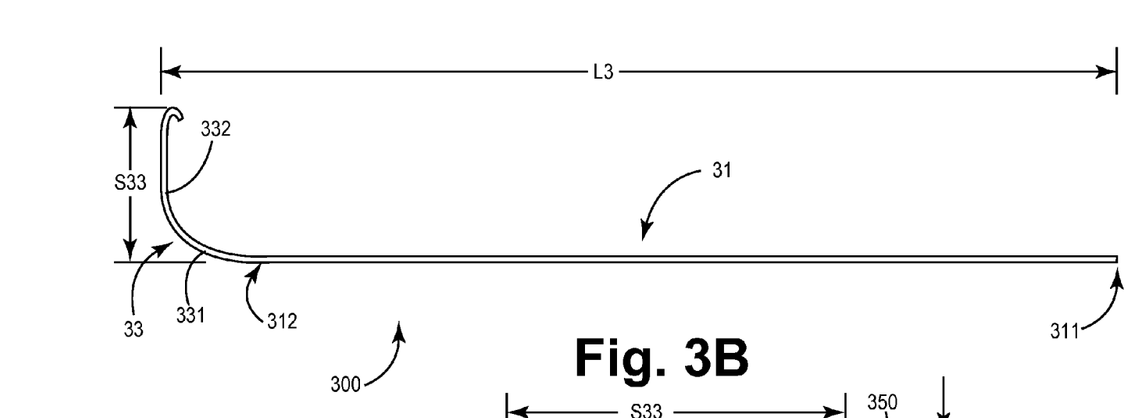
FIGS. 3B-C are plan and end views, respectively, of the catheter shown in FIG. 3A.
Figure 3C:
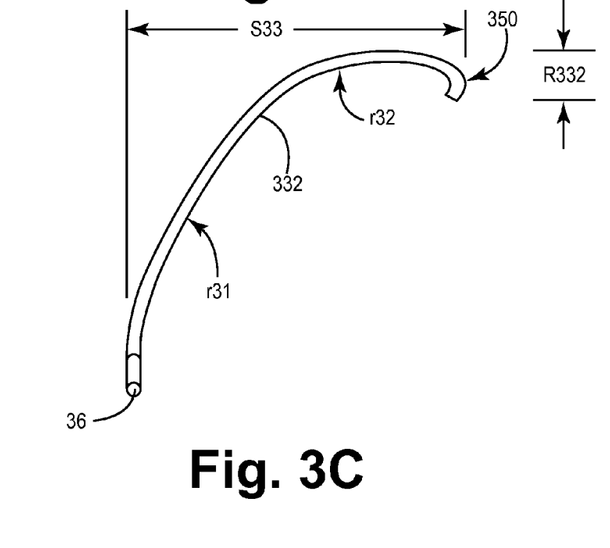

FIGS. 3B-C are plan and end views, respectively, of catheter 300. FIG. 3B illustrates catheter 300 having an effective length L3 and distal segment 33 having a span S33; and FIG. 3C illustrates second curve 332 of segment 33 having a reach R332. With reference back to FIG. 2, it will be appreciated that span S33 and reach R332 provide catheter 300 with a capacity to wrap about the left lateral aspect of heart 100 from the anterior side, and to position tip 350 in zone 105. According to an exemplary embodiment of the present invention: effective length L3 is between approximately 48 cm (19") and approximately 53 cm (21"); a formed radius of first curve 331 is between approximately 15.2 cm (6") and approximately 16.5 cm (6.5"); span S33 is between approximately 7.6 cm (3") and approximately 8.9 cm (3.5"); and reach R332 is between approximately 7.6 cm (3") and approximately 8.1 cm (3.2"). It should be noted that the exemplary dimensions for span S33 and reach R332 are representative of a relaxed state of distal segment 33 and that, since catheter 300 is formed from a resilient material, span S33 and reach R332 of distal segment 33 are likely to expand and/or compress, when catheter 300 is advanced and positioned about a heart, for example, heart 100. With reference to FIG. 3C, second curve 332 may be formed as a simple or compound curve that provides for an appropriate degree of reach R332 while conforming to a general cardiac contour from anterior to posterior about a left lateral side, for example, as illustrated in FIG. 2; according to the exemplary embodiment described above, second curve 332 is compound and has a first radius r31 between approximately 16.8 cm (6.6") and approximately 17.3 cm (6.8"), and a second radius r32 between approximately 4.3 cm (1.7") and approximately 4.8 cm (1.9").

Figure 4A:
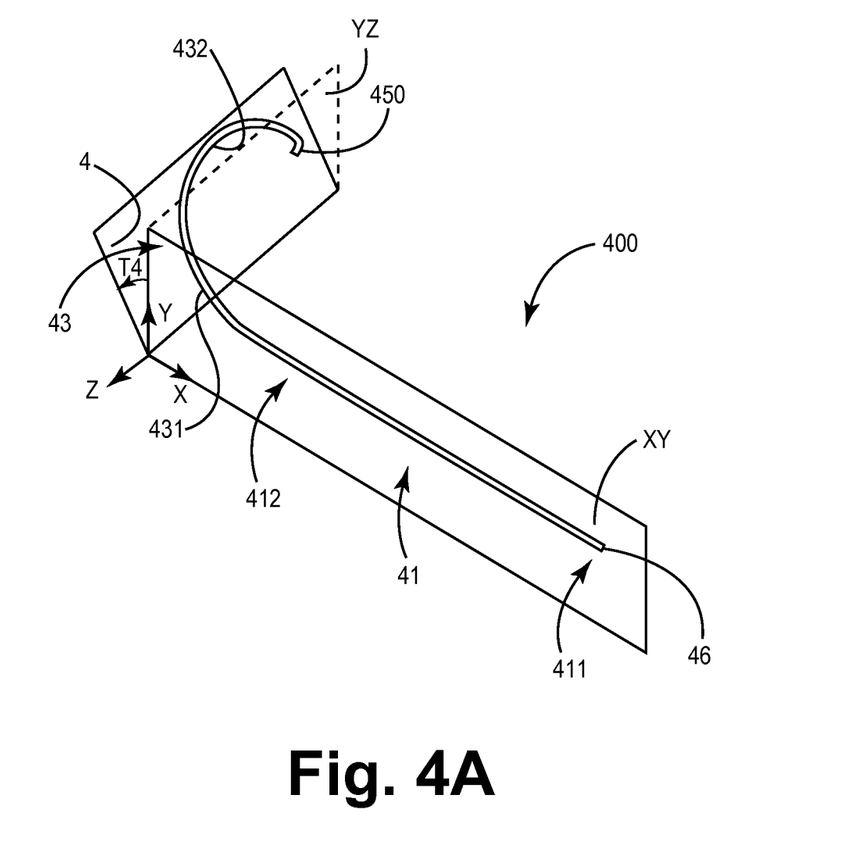
FIG. 4A is perspective view of a delivery catheter, according to some alternate embodiments of the present invention.

FIG. 4A is perspective view of delivery catheter 400, according to some alternate embodiments of the present invention. FIG. 4A illustrates catheter 400 including a relatively straight proximal segment 41, which extends from a proximal end 411 to a distal end 412, and a pre-formed curvature, or curved distal segment 43, which extends from distal end 412 of proximal segment 41. According to the illustrated embodiment, a lumen 46 extends from proximal end 411 through distal tip 450 in order to provide a passageway for delivery of a medical device such as a medical electrical lead. FIG. 4A further illustrates distal segment 43 including a first curve 431 extending in a first plane XY, and a second curve 432 extending in a second plane 4, which is tilted away from plane YZ, per arrow T4, so that second curve 432 extends away from proximal end 411; distal tip 450 is shown extending distally from second curve 432, and, as was previously described for preferred embodiments, is shown formed in a relatively tight bend.

Figure 4B:
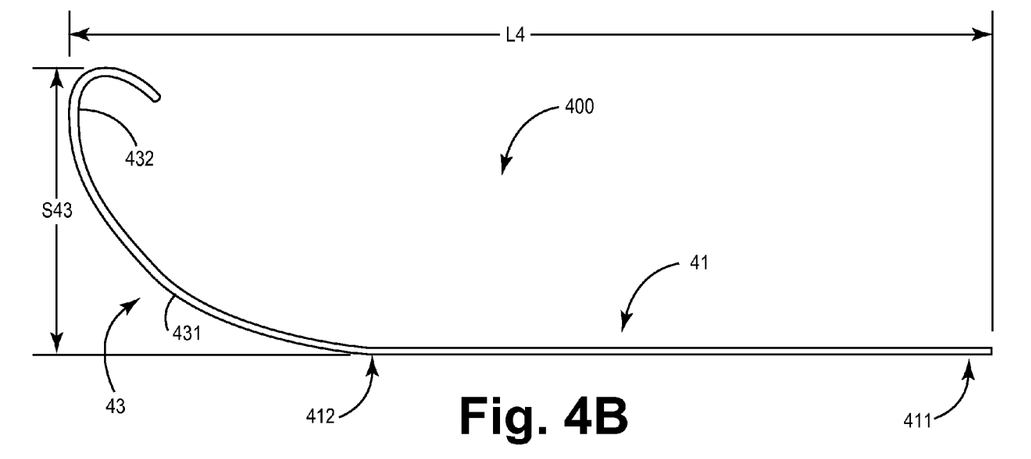
FIGS. 4B-C are plan and end views, respectively, of the catheter shown in FIG. 4A.
Figure 4C:
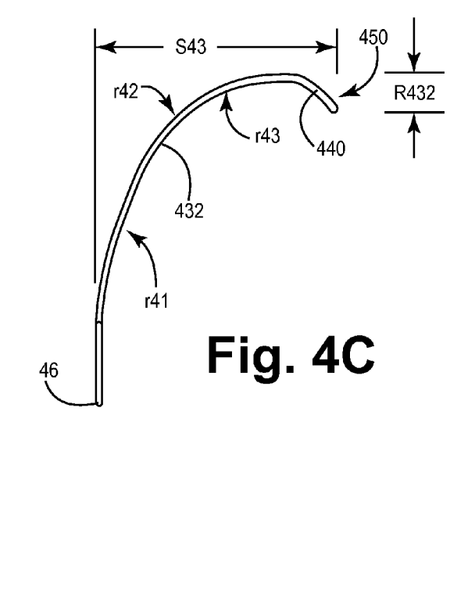

FIGS. 4B-C are plan and end views, respectively, of catheter 400. FIG. 4B illustrates catheter 400 having an effective length L4 and distal segment 43 having a span S43; and FIG. 4C illustrates second curve 432 of segment 43 having a reach R432. With reference back to FIG. 2, it will be appreciated that span S43 and reach R432 provide catheter 400 with a capacity to wrap about the left lateral aspect of heart 100 from the anterior side, and to position tip 450 in zone 105. According to an exemplary embodiment of the present invention: effective length L4 is between approximately 45 cm (17") and approximately 48 cm (19"); a formed radius of first curve 431 is between approximately 18.3 cm (7.2") and approximately 19.6 cm (7.7"); span S43 is between approximately 12.7 cm (5") and approximately 15.2 cm (6"); and reach R432 is between approximately 9.6 cm (3.8") and approximately 10.7 cm (4.2"). It should be noted that the exemplary dimensions for span S43 and reach R432 are representative of a relaxed state of distal segment 43 and that, since catheter 400 is formed from a resilient material, span S43 and reach R432 of distal segment 43 are likely to expand and/or compress, when catheter 400 is advanced and positioned about a heart, for example, heart 100. With reference to FIG. 4C, second curve 432 may be formed as a simple or compound curve that provides for an appropriate degree of reach R432, while conforming to a general cardiac contour from anterior to posterior about a left lateral side, for example, as illustrated in FIG. 2; according to the exemplary embodiment described above, second curve 432 is compound and has a first radius r41 between approximately 9.4 cm (3.7") and approximately 10.4 cm (4.1"), a second radius r42 between approximately 5 cm (2") and approximately 6.1 cm (2.4"), and a third radius r43 between approximately 2.3 cm (0.9") and approximately 3.3 cm (1.3"). FIG. 4C further illustrates distal tip 450 including an optional straight segment 440.

Figure 5A:
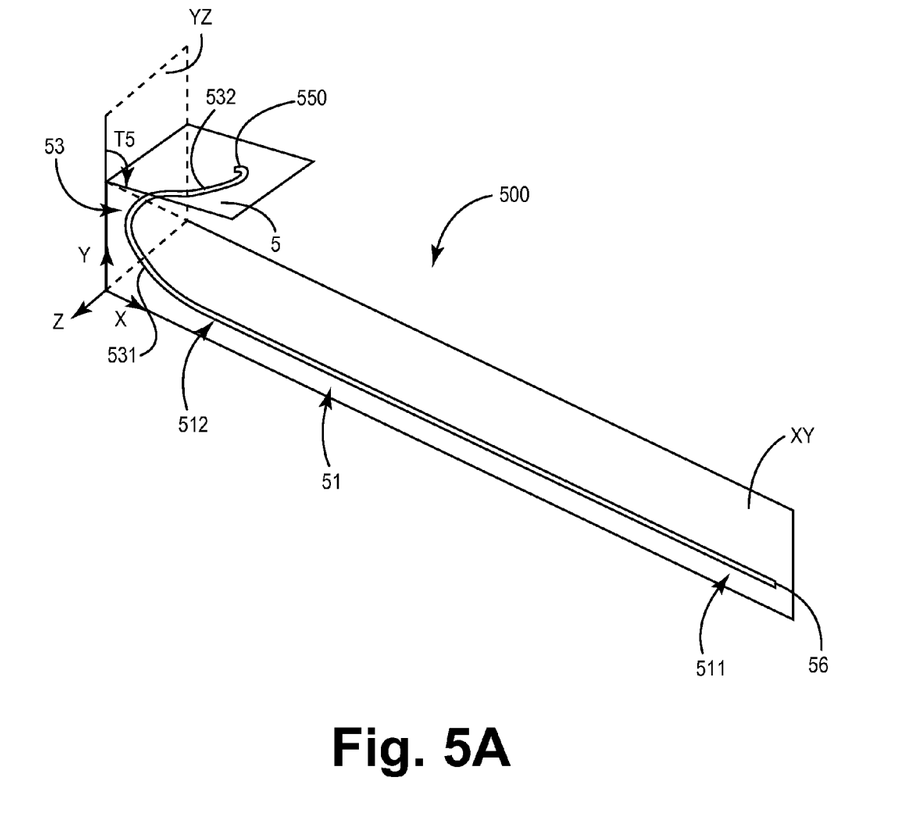
FIG. 5A is perspective view of a delivery catheter, according to yet further embodiments of the present invention.

FIG. 5A is perspective view of delivery catheter 500, according to yet further embodiments of the present invention. FIG. 5A illustrates catheter 500 including a relatively straight proximal segment 51, which extends from a proximal end 511 to a distal end 512, and a pre-formed curvature, or curved distal segment 53, which extends from distal end 512 of proximal segment 51. According to the illustrated embodiment, a lumen 56 extends from proximal end 511 through distal tip 550 in order to provide a passageway for delivery of a medical device such as a medical electrical lead. FIG. 5A further illustrates distal segment 53 including a first curve 531 extending in a first plane XY, and a second curve 532 extending in a second plane 5, which is tilted away from plane YZ, per arrow T5, so that second curve 532 extends toward proximal end 511; distal tip 550 is shown extending distally from second curve 532, and, as was previously described for preferred embodiments, is shown formed in a relatively tight bend.

Figure 5B:
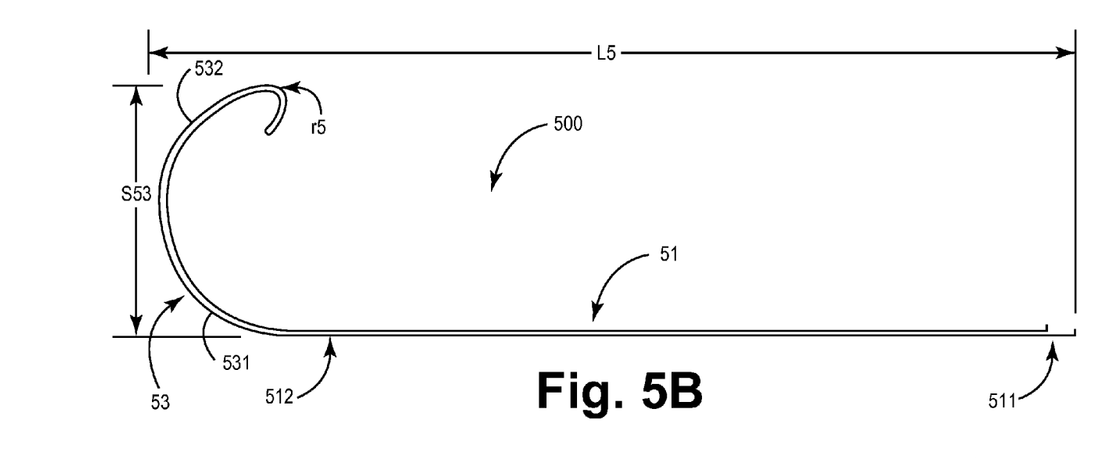
FIGS. 5B-C are plan and end views, respectively, of the catheter shown in FIG. 5A.
Figure 5C:
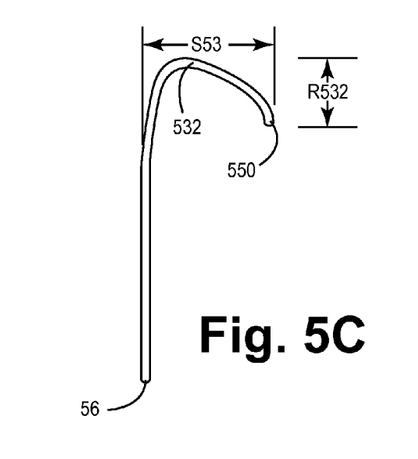

FIGS. 5B-C are plan and end views, respectively, of catheter 500. FIG. 5B illustrates catheter 500 having an effective length L5 and distal segment 53 having a span S53; and FIG. 5C illustrates second curve 532 of segment 53 having a reach R532. With reference back to FIG. 2, it will be appreciated that span S53 and reach R532 provide catheter 500 with a capacity to wrap about the left lateral aspect of heart 100 from the anterior side, and to position tip 550 in zone 105. According to an exemplary embodiment of the present invention: effective length L5 is between approximately 43 cm (17") and approximately 48 cm (19"); a formed radius of first curve 531 is between approximately 5.8 cm (2.3") and approximately 6.9 cm (2.7"); span S53 is between approximately 11.4 cm (4.5") and approximately 14 cm (5.5"); and reach R532 is between approximately 4.3 cm (1.7") and approximately 5.4 cm (2.1"). It should be noted that the exemplary dimensions for span S53 and reach R532 are representative of a relaxed state of distal segment 53 and that, since catheter 500 is formed from a resilient material, span S53 and reach R532 of distal segment 53 are likely to expand and/or compress, when catheter 500 is advanced and positioned about a heart, for example, heart 100. With reference to FIG. 5C, second curve 532 may be formed as a simple or compound curve that provides for an appropriate degree of reach R532, while conforming to a general cardiac contour from anterior to posterior about a left lateral side, for example, as illustrated in FIG. 2; according to the exemplary embodiment described above, second curve 532 is simple, having a radius r5 between approximately 2.3 cm (0.9") and approximately 2.8 cm (1.1").

In the foregoing detailed description, the invention has been described with reference to specific embodiments. However, it may be appreciated that various modifications and changes can be made without departing from the scope of the invention as set forth in the appended claims.

We claim:

1. A delivery catheter including a longitudinally extending lumen for passage of a medical device therethrough, the catheter comprising:
   a relatively straight proximal segment including a proximal end and a distal end; and
   a pre-formed and resilient heart-wrapping segment extending from the distal end of the proximal segment;
   wherein the heart-wrapping segment includes a first curve extending distally from the proximal segment in a first plane a distance of from between approximately 7.6 cm and approximately 15.2 cm and a second curve extending from the first curve in a second plane a distance of between approximately 4.3 cm and approximately 10.7 cm, wherein the second curve is a compound curve.

2. The catheter of claim 1, wherein the first curve has a formed radius between approximately 5.8 cm and approximately 19.6 cm.

3. The catheter of claim 1, further comprising a distal tip extending distally from the second curve and formed in a bend having a formed radius less than approximately 2 cm.

4. The catheter of claim 1, wherein the second plane is approximately orthogonal to the first plane.

5. The catheter of claim 1, wherein the first curve extends in the first plane a distance of between approximately 7.6 cm and approximately 8.9 cm.

6. The catheter of claim 1, wherein the first curve has a formed radius between approximately 15.2 cm and approximately 16.5 cm.

7. The catheter of claim 1, wherein the second curve extends in the second plane a distance of between approximately 7.6 cm and approximately 8.1 cm.

8. The catheter of claim 1, further comprising a distal tip extending distally from the second curve and formed in a bend having a formed radius less than approximately 2 cm.

9. The catheter of claim 1, wherein the second curve extends away from the proximal end of the proximal segment in the second plane.

10. The catheter of claim 9, wherein the first curve extends in the first plane a distance of between approximately 12.7 cm and approximately 15.2 cm.

11. The catheter of claim 9, wherein the first curve has a formed radius between approximately 18.3 cm and approximately 19.6 cm.

12. The catheter of claim 9, wherein the second curve extends in the second plane a distance of between approximately 9.6 cm and approximately 10.7 cm.

13. The catheter of claim 9, further comprising a distal tip extending distally from the second curve and formed in a bend having a formed radius less than approximately 2 cm.

14. The catheter of claim 9, further comprising a distal tip extending distally from the second curve, the distal tip including a relatively straight segment.

15. The catheter of claim 1, wherein the second curve extends toward the proximal end of the proximal segment in the second plane.

16. The catheter of claim 15, wherein the first curve extends in the first plane a distance of between approximately 11.4 cm and approximately 14 cm.

17. The catheter of claim 15, wherein the first curve has a formed radius between approximately 5.8 cm and approximately 6.9 cm.

18. The catheter of claim 15, wherein the second curve extends in the second plane a distance of between approximately 4.3 cm and approximately 5.4 cm.

19. The catheter of claim 15, further comprising a distal tip extending distally from the second curve and formed in a bend having a formed radius less than approximately 2 cm.

20. A delivery catheter including a longitudinally extending lumen for passage of a medical device therethrough, the catheter comprising
   a distal segment having a pre-formed curvature for wrapping around a left side of a heart from an anterior epicardial surface to a posterior epicardial surface, when the catheter is advanced along the epicardial surface, having been inserted from a sub-xyphoid access site; and
   a distal tip extending distally from the distal segment;
   wherein the curvature of the distal segment facilitates a positioning of the distal tip along a posterior lateral aspect of the epicardial surface in proximity to a base of the left side of the heart when the curvature wraps about the heart and wherein the curvature of the distal segment extends a distance of between approximately 7.6 cm and approximately 15.2 cm in a first plane and extends a distance of between approximately 4.3 cm and approximately 10.7 cm in a second plane, wherein the curvature extending in the second plane is a compound curve.

21. The catheter of claim 20, wherein the distal tip is formed in a bend such that an outer surface of the bend is a leading edge of the catheter, when the curvature of the distal segment is straightened and the catheter is initially advanced along the epicardial surface.

22. The catheter of claim 21, wherein the bend has a formed radius of less than approximately 2 cm.

23. The catheter of claim 20, wherein the distal tip is formed in a bend such that an outer surface of the bend is a leading edge of the catheter, when the curvature of the distal segment is straightened and the catheter is initially advanced along the epicardial surface.

24. The catheter of claim 23, wherein the bend has a formed radius of less than approximately 2 cm.

25. The catheter of claim 20, wherein the curvature of the distal segment extends a distance between approximately 7.6 cm and approximately 15.2 cm.

* * * * *